US008013595B2

(12) United States Patent
Jones et al.

(10) Patent No.: US 8,013,595 B2
(45) Date of Patent: Sep. 6, 2011

(54) AC MAGNETIC TRACKING SYSTEM WITH PHASE LOCKING

(75) Inventors: Herbert R. Jones, Williston, VT (US); Robert F. Higgins, South Burlington, VT (US); Henry E. Himberg, Williston, VT (US)

(73) Assignee: ALKEN Inc., Colchester, VT (US)

( * ) Notice: Subject to any disclaimer, the term of this patent is extended or adjusted under 35 U.S.C. 154(b) by 716 days.

(21) Appl. No.: 12/157,725

(22) Filed: Jun. 12, 2008

(65) Prior Publication Data

US 2009/0030646 A1    Jan. 29, 2009

Related U.S. Application Data

(60) Provisional application No. 60/934,356, filed on Jun. 13, 2007.

(51) Int. Cl.
*G01B 7/14* (2006.01)
*G01R 33/12* (2006.01)
(52) U.S. Cl. ............... 324/207.17; 324/244; 324/247; 348/448

(58) Field of Classification Search ............... 324/244, 324/247, 207.17; 342/448
See application file for complete search history.

(56) References Cited

U.S. PATENT DOCUMENTS

| 6,762,600 B2 | 7/2004 | Khalfin |
| 7,015,859 B2 | 3/2006 | Anderson |
| 7,096,148 B2 | 8/2006 | Anderson et al. |
| 7,174,202 B2 | 2/2007 | Bladen et al. |
| 2005/0285590 A1 | 12/2005 | Higgins et al. |
| 2007/0164895 A1 | 7/2007 | Anderson |

OTHER PUBLICATIONS

International Search Report, PCT/US08/07373, Sep. 25, 2008.

*Primary Examiner* — Reena Aurora
(74) *Attorney, Agent, or Firm* — Lerner, David, Littenberg, Krumholz & Mentlik, LLP

(57) ABSTRACT

Plural transmitter coils of a magnetic locating system are driven with widely-separated main frequencies. One of the transmitter coils is also driven with a marker frequency close to the main frequency applied to that coil. The receiver determines a phase relationship with the transmitter based on the main and marker frequencies, so that the receiver does not suffer from phase ambiguity. The main and marker frequencies may interfere with one another, and the receiver may correct for such interference based on known characteristics of the signals at the main and marker frequencies.

31 Claims, 3 Drawing Sheets

AC MAGNETIC TRACKING SYSTEM WITH PHASE LOCKING

CROSS-REFERENCE TO RELATED APPLICATIONS

The present application claims benefit of the filing date of U.S. Provisional Patent Application No. 60/934,356, filed Jun. 13, 2007, the disclosure of which is incorporated by reference herein.

FIELD OF THE INVENTION

The present invention relates to magnetic locators, commonly also referred to as magnetic tracking systems.

BACKGROUND OF THE INVENTION

A magnetic tracking system includes a sender or transmitter which applies magnetic fields in space, and a sensor which detects the fields. Most commonly, the transmitter includes three coils directed along three mutually orthogonal axes. Typically, these coils are co-located, i.e., wound so that their centers are at or very near to the same point in space. The sensor or receiver typically includes a similar assembly of three coils or other sensors. The position and orientation of the receiver in the frame of reference of the transmitter can be determined from the set of relationships between each transmitter coil and each coil or sensor of the receiver. Thus, each transmitter coil is actuated to emit a magnetic field and the resulting magnetic field component in the direction of each receiver coil or other sensor is measured by the receiver.

Magnetic locating systems of this type are used in many applications. For example, the receiver may be attached to a surgical instrument so that the instrument can be tracked in the frame of reference of the operating room, or in the frame of reference of a previously acquired image of the patient. Also, a probe having a receiver mounted thereon can cooperate with a fixed transmitter so that as the probe is moved over the surface of a three-dimensional object, the contours of the object are deduced from the position of the probe. In still other applications, the sensor may be mounted on a part of a human body and used to measure the position and orientation of that body part relative to a frame of reference holding the transmitter. For example, a head-mounted sensor can be used to detect the direction in which a user has turned his or her head. In still other arrangements, a receiver may serve as a three-dimensional input tool for a computer or computer game. Although the various applications have been described with reference to a moving receiver and a fixed transmitter or sender, these can be reversed, so that the transmitter moves in the frame of reference of the sensor.

In a frequency-multiplexed AC system, each of the transmitter coils is driven at a different frequency, most commonly with a continuous sinusoidal signal at such frequency. If the sensor is in an arbitrary orientation relative to the transmitter, the axes of the sensor coils will not be aligned with the axes of the transmitter coils. In this case, each sensor coil detects the magnetic fields generated by all of the transmitter coils, so that each sensor coil delivers a composite coil signal which includes components at each of the transmitted frequencies.

The components in each sensor signal are separated from one another by techniques such as filtering or, most commonly, Fourier transformation of the sensor signal to yield a frequency domain representation. The separated components provide nine separate components, each of which represents the signal induced in one sensor coil by one transmitter coil. For example, there is a component $S_{XY}$ representing the signal induced on the sensor coil oriented in the X-direction of the receiver by the field from the coil oriented in the Y-direction of the transmitter. Similarly, there is a signal $S_{XX}$ representing the signal induced in the sensor coil oriented in the X-direction of the receiver by the field emitted from the coil oriented in the X-direction of the transmitter.

The position and orientation of the sensor in the frame of reference of the transmitter can be computed from the phase and amplitude of the various components. Algorithms for accomplishing this are shown, for example, in Jones, U.S. Pat. No. 4,737,794; Egli et al., U.S. Pat. No. 4,287,809; and Raab, U.S. Pat. No. 4,314,251, the disclosures of which are hereby incorporated by reference herein.

However, the phase of the received signal components relative to the phase of the transmitted field components must be known. In a "wired" system, the receiver is connected to the transmitter, so that the receiver operates in synchronism with the transmitter. Therefore, the receiver can directly determine the phase of the sensor signal components using the same timing reference employed by the sender.

In some applications, however, a wire or other direct connection between the sender and the sensor is undesirable or impractical. Therefore, wireless systems have been developed. Examples of wireless systems are disclosed in U.S. Published Patent Application No. 2005/0285590 ("the '590 Publication") and in Anderson, U.S. Pat. No. 7,015,859 ("the '859 patent"). In a wireless system, the receiver is not synchronized with the transmitter unit. In general, the receiver cannot detect the phase of the signals used to drive the transmitter coils without ambiguity. For example as the sensor moves past the center point of the transmitter in one of the three directions constituting the frame of reference of the transmitter, the sign of a signal component reverses. This reverses the phase of the signal component in exactly the same manner as if the phase of the signal used to drive a transmitter coil was shifted 180° or $\pi$ radians.

As disclosed in the aforementioned '590 publication, one solution to this problem is to calibrate the receiver while it is at a known position and orientation relative to the transmitter. By imposing this known start-up geometry on the system, the receiver can determine the phase relationship between the transmitter and the timing reference used by the receiver.

Another approach disclosed in the aforementioned '859 patent uses a drive signal for one or more transmitter coils, which includes a main drive frequency, and the second harmonic of the main frequency. The second harmonic is in-phase with the main frequency only once in each cycle of the main frequency. In the example shown in the '859 patent, the second harmonic has a positive-going peak synchronized with the positive-going peaks of the main signal, but not with the negative-going peaks of the main signal. Thus, by monitoring the sensor signal components at the main and harmonic frequencies, and noting when the two are in synchronization (as, for example, when both have a positive-going peak), the receiver can unambiguously determine the phase of the transmitter signal at the main frequency. While this approach can resolve the 0 or $\pi$ phase ambiguity, it suffers from a serious drawback. Typically, each coil of a field transmitter is driven by a resonant circuit which includes the inductance of the coil and a capacitance. These components are selected so that the resulting circuit will be in-resonance at the main frequency, and hence, will efficiently generate magnetic fields when driven with a signal at the main frequency. These components are also designed to have a high "Q" value. Q is a measure of the quality of a resonant circuit. A circuit with a high Q value has a narrow bandwidth. That is, the circuit can be driven very efficiently within a narrow band of frequencies encompassing the resonant frequency of the circuit, but is very inefficient at frequencies outside this band. By definition, the second harmonic is at a frequency double the main frequency. If the resonant circuit must operate at both of these frequencies the resonant circuit have a relatively low Q, and hence, a large bandwidth. This sacrifices efficiency at the main frequency, leading to higher power consumption. Although a separate resonant circuit can be added to generate fields at the second harmonic, this considerably increases the complexity and cost of the transmitter.

Accordingly, further improvement would be desirable.

SUMMARY OF THE INVENTION

One aspect of the invention provides magnetic locating apparatus. Apparatus according to this aspect of the invention desirably includes a transmitter which has a plurality of co-located orthogonal transmitter coils. The transmitter desirably also includes a transmitter circuit operative to apply a signal to each transmitter coil including a main sinusoidal component having a main frequency $f_B$, where B is an index denoting one of said transmitter coils, $f_B$ being different for different transmitter coils. Most preferably, the transmitter circuit is also operative to drive a particular one of the transmitter coils (denoted by index B*) with a sinusoidal marker component having a known amplitude and phase relationship to the main component transmitted by the same coil. The marker component most preferably has a frequency $f'_{B*}$ such that the difference between $f_{B*}$ and $f'_{B*}$ is smaller than the difference between any two of the main frequencies $f_B$. For example, the frequencies may be selected so that for all of the coils $f_B = n_B/T_S$, where $n_B$ is an integer, and $f'_{B*} = n'_{B*}$, where $n'_{B*}$ is an integer. Desirably, $n'_{B*}$ and $n_{B*}$ differ by one.

The apparatus desirably also includes a receiver having a plurality of co-located orthogonal sensor coils. The coils yield a plurality of sensor signals responsive to magnetic fields sent by the transmitter. The receiver desirably includes a receiver circuit operative to process the sensor signals to derive separate components $S_{AB}$ in each sensor signal at each main frequency $f_B$ where A is an index denoting one of the sensor coils and to derive a separate component $S'_{AB*}$ in at least one sensor signal at a marker frequency $f'_{B*}$. The receiver circuit desirably is operative to determine the phase of at least one component in at least one sensor signal from sensor signal components $S_{A*B*}$ and $S'_{A*B*}$, where A* is a particular index A and B* is a particular index B. The receiver circuit desirably is arranged to compute the position of the sensor coils relative to the transmitter coils based on the determined phase and on the components $S_{AB}$.

Because the main and marker signal components applied to a given transmitter coil are close in frequency, a high-Q resonant circuit can apply both components with good efficiency. The frequency difference between main and marker components may be smaller than the frequency resolution of the receiver, causing the main and marker components to interfere with one another. However, as further explained below, the system can correct for this interference based on known relationships between the main and marker components and known properties of the receiver.

Further aspects of the invention include methods of magnetic locating using steps similar to operation of the apparatus discussed above.

These and other objects, features and advantages of the invention will be more readily apparent from the detailed description set forth below, taken in conjunction with the drawings.

DETAILED DESCRIPTION

Figure 1:
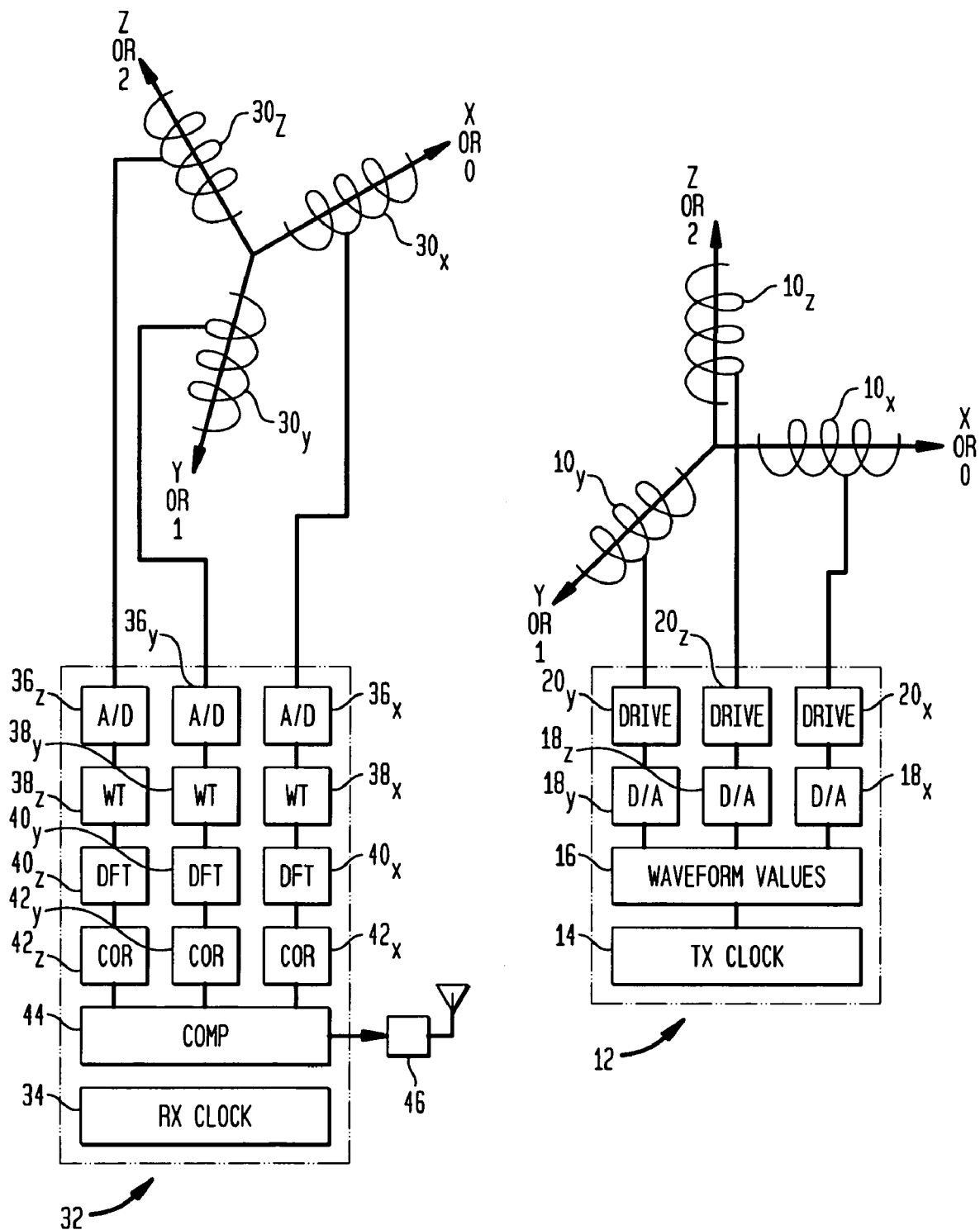
FIG. 1 is a functional block diagram of apparatus in accordance with one embodiment of the invention.

In the description below and the accompanying drawings, functional elements of the receiver are shown and described as separate circuits for ease of understanding. Likewise, functional elements of the transmitter are shown and described as separate circuits. However, this should not be taken as requiring separate physical components. For example, a programmable component such as a microprocessor or ASIC may be arranged to fulfill the roles of different circuit elements at different times, and a single component may serve as part or all of two or more of the functionally-described separate circuits.

A transmitter in accordance with one embodiment of the invention includes a set of three collocated coils $10_X$, $10_Y$ and $10_Z$ disposed along three mutually orthogonal axes, arbitrarily labeled "X," "Y," and "Z" (or, alternatively, 0, 1, and 2, respectively). The axes of the coils define a conventional Cartesian coordinate system or frame of reference. Although the coils are shown as separated from one another for clarity of illustration, in practice, the coils desirably have their centers as close as practicable to a common central point. The transmitter further includes a transmitter control circuit 12, which is adapted to drive each of the coils with sinusoidal oscillations as discussed below. In the particular embodiment depicted, the transmitter control circuit includes a digital transmitter clock 14 and a waveform value circuit 16. Waveform value circuit 16 may be a conventional microprocessor arranged to calculate the successive values which constitute the desired sinusoidal waveforms. Alternatively, the waveform value unit circuit may include a memory with the successive values constituting each waveform stored at known addresses, so that the successive values will be read out in sequence when the memory is clocked by transmitter clock 14.

The waveform value circuit 16 is connected to a set of three digital-to-analog converters 18, one associated with each coil 10 of the transmitter. These connections are arranged so that the successive values which constitute the waveforms to be applied to coil $10_X$ are sent to the associated D/A converter $18_X$, and so on. Each D/A converter 18 is connected to a drive circuit 20, which in turn, is connected to one coil 10. The drive circuit is arranged to energize the associated coil, so as to drive the coil in oscillations and provide sinusoidally varying magnetic fields in accordance with the applied waveforms. For example, the drive circuits may include elements such as power amplifiers, and typically also include capacitance connected in circuit with the associated coil so as to form a resonant circuit. Each such resonant circuit desirably is resonant at the frequency of the waveform applied to that coil, and has a relatively high-Q value and narrow bandwidth.

Figure 2:
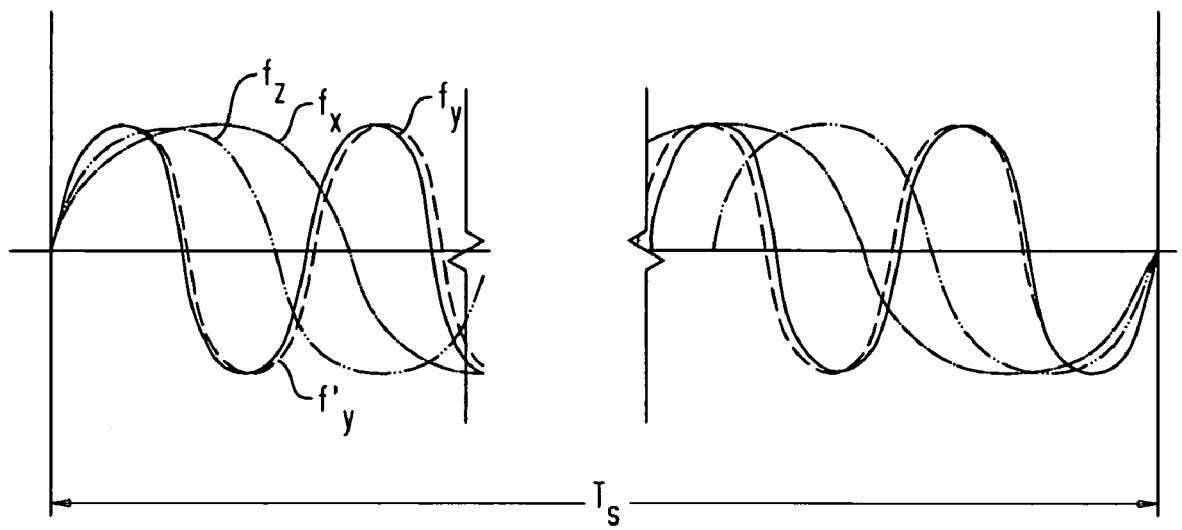
FIG. 2 is a diagrammatic representation of certain signals used by the transmitter in the apparatus of FIG. 1.

The waveforms applied to the transmitter coils are based on a frame interval or sampling interval $T_S$ (FIG. 2). The excitation applied to each coil $10_X$, $10_Y$, and $10_Z$ includes a main drive frequency $f_X$, $f_Y$, or $f_Z$, respectively. Each of these main drive frequencies is selected so that there are an integral number of periods of the sinusoidal waveform at the drive frequency in the frame or sampling interval $T_S$. Stated another way, $f_B = n_B/T_S$, where B is an index denoting the transmitter coil; $f_B$ is the main drive frequency applied to that transmitter coil; and $n_B$ is an integer associated with the particular drive coil B. The value of $n_B$ is different for each different drive coils. The term "frequency bin" is used herein to refer to a value of $n_B$. That is, two waveforms having $n_g$ different by 1 are said to differ by 1 frequency bin. The main drive frequencies $f_X$, $f_Y$, and $f_Z$ are widely separate from one another separated from one another by several bins, typically at least about 4 bins. Stated another way, the difference between the bin numbers or $n_B$ for any two main drive frequencies $f_B$ is substantial, so that there is a substantial difference between the main drive frequencies. This facilitates separation of components at the different main drive frequencies at the receiver.

Although the particular parameters of different systems can vary over a substantial range, one exemplary system uses a frame or sample interval $t_S$ of 4.166 milliseconds and a maximum drive frequency of 27.84 kilohertz corresponding to n=116, or 116 periods of the waveform in each interval $T_S$. Each bin corresponds to as frequency difference of about 240 Hz. In the exemplary system, the main drive frequencies $f_X$, $f_Y$, and $f_Z$ are separated from one another by four bins. As further discussed below, this relatively wide separation facilitates separation of components at the main drive frequency by filtering or Fourier transformation. Notably, because the main drive frequencies are applied to separate coils through separate resonant circuits $20_X$, $20_Y$, and $20_Z$, the wide separation between main drive frequencies does not pose a problem; each drive circuit is tuned to approximately the particular drive frequency used with that coil.

All of the waveforms at the main drive frequencies are coordinated to be in-phase or aligned with one another at the beginning of the frame or sampling interval $T_S$ used by the transmitter. As seen in FIG. 2, at the beginning or 0 point of the sampling interval, all of the waveforms at main drive frequencies $f_X$, $f_Y$, and $f_Z$ are at zero phase, i.e., 0 amplitude and increasing. Because there are an integral number of periods of each main drive frequency in the sampling interval, all of the main drive frequencies are also in-phase with one another at the end of the sampling period $T_S$. Two or three main drive frequencies typically will also be aligned with each other at intermediate points (not shown) within $T_S$.

The oscillations applied to one of the drive coils—in this instance, the Y drive coil $10_Y$—also include a sinusoidal waveform at an additional frequency $f'_Y$, referred to for convenience in this disclosure as the "marker" frequency. The marker frequency likewise has an integral number of periods in the sampling interval T, i.e., the marker frequency is selected as: $f'_Y = n'_B/T_B$, where $n'_B$ is an integer. The marker frequency desirably differs from the main drive frequency applied to the same transmitter coil by only 1 bin. That is, the absolute value of $(n_B - n'_B)$ is equal to 1. As best appreciated with reference to FIG. 2, the oscillations at the marker frequency $f'_Y$ are aligned with the oscillations at the main drive frequency $f_Y$ only at the beginning and end of a sample interval $t_S$. Stated another way, the phase difference between the oscillations at $f_Y$ and at $f'_Y$ varies sinusoidally at a rate equal to the frequency separation between $f_Y$ and $f'_Y$. Since this frequency separation is equal to the frame rate or $1/T_S$, the phase difference is zero only at the beginning of the sampling interval $t_s$ as applied by the transmitter.

Because the marker frequency and main frequency applied to drive coil Y are very close to one another, the coil can be driven efficiently with both frequencies, i.e., with a composite signal including both frequencies. Stated another way, both the marker frequency and the main drive frequency are within the bandwidth of the high-Q resonance circuit incorporated in drive circuit $20_Y$.

The receiver (FIG. 1) includes a set of three collocated sensors in the form of coils $30_X$, $30_Y$, and $30_Z$. Like the transmitter coils, the receiver or sensor coils $30_X$, $30_Y$, and $30_Z$ are oriented along three orthogonal axes denoted X, Y, or Z (or equivalently, 0, 1, or 2). However, because the receiver is free to move relative to the transmitter, the X, Y, and Z axes of the receiver lie at an unknown orientation in the frame of reference of the transmitter coils 10.

Each receiver coil generates an electrical signal representing the magnetic fields impinging on that coil. Typically, each receiver coil will generate a signal which includes components varying at all of the frequencies emitted by the various transmitter coils. The notation $S_{AB}$ is used in this disclosure to designate the components in the various sensor signals, where A is an index denoting the particular sensor coil which received the component, and B is an index denoting one of the transmitter coils, and hence one of the main drive frequencies. For example, the signal from X-direction coil $30_X$ will include component $S_{XX}$ at main drive frequency $f_X$ applied to X-direction coil $10_X$, component $S_{XY}$ at main drive frequency $f_Y$, and a component $S_{XZ}$ at main drive frequency $f_Z$. The signal supplied by each receiver coil 10 will also include a component denoted herein as $S'_{AB}$ at each marker frequency, where again, A is the index denoting the receiver coil and B is an index denoting the transmitter coil from which the marker frequency signal is sent. In the particular embodiments depicted in FIGS. 1 and 2, a marker frequency is applied only to the Y-direction coil of the transmitter. Therefore, the signal from receiver coil $30_X$ will include a component $S'_{XY}$, in addition to the main frequency components $S_{XX}$, $S_{XY}$, and $S_{XZ}$. Each of the signals from the other coils will include a similar set of components.

The receiver includes a receiver circuit 32 connected to the coils. The receiver circuit includes a receiver clock 34 and analog-to-digital converters $36_X$, $36_Y$, and $36_Z$ linked to coils $30_X$, $30_Y$, and $30_Z$, respectively. The A/D converters 36 operate at a sample rate substantially higher than the main or drive frequencies. For example, in an embodiment where the main frequencies are on the order of 27.84 kHz, the sampling rate may be on the order of 96 kHz. Thus, each A/D converter 36 provides a series of digital samples in time, representing the composite waveform received by the associated coil 30.

The receiver control circuit 32 also includes windowing or weighting circuits $38_X$, $38_Y$, and $38_Z$. The windowing circuits subdivide the successive samples into small sets, each representing a very short interval or "window" and apply a weighting function to the samples within each set based on the timing of the samples within the window. In general, a weighting function multiples the digital value of each sample by a coefficient which depends on the timing of each sample. Weighting or windowing functions of this type are well-known in the art of digital signal processing. In general, the object of a waiting function is to treat the samples in such a manner that the response of a discrete Fourier transform applied to the samples will be reasonably consistent over a wide range of frequencies. Without a windowing function, the Fourier transform has a very pronounced response to signals having a frequency which is an integral multiple of the frame rate, but has a broad, flat response, and hence, little frequency discrimination capability, for signals which deviate from such an integral multiple. With a windowing function applied to the samples in the time domain before the samples are provided to the discrete Fourier transform, the transform yields a reasonably sharp response for all frequencies. One example of such a waiting function is the well-known Blackman-Harris windowing function.

Figure 3:
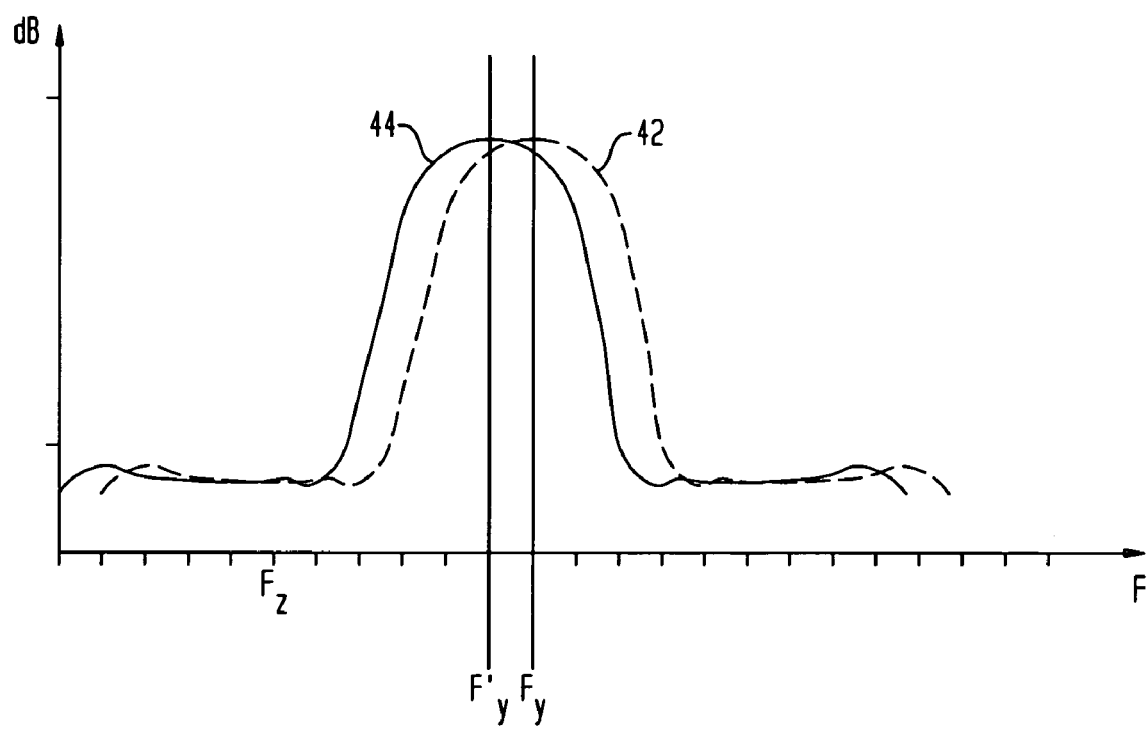
FIG. 3 is a diagrammatic representation of the response of certain components in the receiver.

The receiver control circuit further includes discrete Fourier transform ("DFT") circuits $40_X$, $40_Y$, and $40_Z$, which receive the windowed time domain data, perform a discrete Fourier transform on the time domain data and outputs representations of components at frequencies corresponding to the frequency bins discussed above, i.e., at discrete frequencies corresponding to $n/T_S$ where n is an integer. The combination of the windowing function and the DFT yields a transfer function illustrated diagrammatically in FIG. 3. The response curve for a signal component at $f_Y$ is illustrated by curve 42 in broken lines. When the time-domain data includes a signal component at $f_Y$, the DFT yields a representation of a component at $f_Y$ having a relatively large amplitude. However, response curve 42 has substantial magnitude at other discrete frequencies separated from frequency $f_Y$ by less than about four bins, including at $f'_Y$. Thus, when the time-domain data includes a signal component at $f_Y$ the DFT circuit will yield a representation of a component with substantial magnitude at $f'_Y$ as well. Likewise, curve 44 in solid lines represents the response of the combined windowing and DFT circuits to a signal at marker frequency $f'_Y$; the response will include substantial components at both $f'_Y$ and $f_Y$. Accordingly, if a signal incorporating data representing a composite of $f_Y$ and $f'_Y$ is presented to the windowing and DFT circuits, these circuits will yield a component at $f_Y$ which represents a composite of the signals at $f'_Y$ and $f_Y$. Likewise, the DFT circuit will provide a component at frequency $f'_Y$, which is actually a represents the signals at $f_Y$ and $f'_Y$.

Stated another way, the main frequency and marker frequency applied to a particular transmitter coil, such as $f'_Y$ and $f_Y$, are separated from one another by a difference in frequency less than the frequency resolution of the receiver. Likewise, the components representing this main frequency and marker frequency in the signals from a particular coil will also be separated from one another by less than the frequency resolution of the system. Thus, the component at the marker frequency and the component at the main frequency interfere with one another. By contrast, the different main drive frequencies $f_Y$, $f_X$, and $f_Z$ are separated from one another by a frequency separation larger than the frequency resolution of the system.

The receiver control circuit 32 also includes correction circuits 42x, 42y and 42z which compensate for the interference between the main frequency and marker frequency. Within a given sensor signal, the components at the main frequency and marker frequency represent signals sent over the same signal path between a single transmitter coil 10 and a single sensor coil 30. For example, component $S_{YY}$ and $S'_{YY}$ both represent signals sent between transmitter coil 10y and sensor coil 30y. Thus, the amplitude and phase relationship between the transmitter drive signal at main frequency $f_Y$ and the transmitter drive signal at marker frequency $f'_Y$ as applied to transmitter coil $10_Y$ is preserved in components $S_{YY}$ and $S'_{YY}$. As the amplitude and phase relationship of the transmitter drive signals is known, corrected signal components for any sensor coil A* receiving main and marker frequencies from a particular transmitter coil B* can be derived from the following relationships:

$$S_{A*B*UNCORRECTED} = S_{A*B*CORRECTED} + K_1 (S'_{A*B*CORRECTED})$$

$$S'_{A*B*UNCORRECTED} = S'_{A*B*CORRECTED} + K_2 (S_{A*B*CORRECTED})$$

where $K_1$ and $K_2$ are constants which are derived from the relationship between the transmitter drive signals and the transfer function of the combined window and DFT circuits. In the particular case shown in FIG. 2, where the transmitter drive signals at the main and marker frequencies are of equal in amplitude, $K_1=K_2$. In this case, each constant K is simply the inverse of the ratio between (i) the transfer function relating output at a given frequency to input data at that frequency and (ii) the transfer function relating output one bin over from the given frequency to the same input data. In the embodiment shown, the corrections are applied only to signals at $f_Y$ and $f'_Y$ (i.e., $S_{XY}$; $S'_{XY}$; $S_{YY}$; $S'_{YY}$; $S_{ZY}$; and $S'_{ZY}$) as the other drive frequencies do not suffer from appreciable interference.

The receiver control circuit 32 further includes a computation circuit 44 arranged to perform the computations discussed below. The components $S_{AB}$ and $S'_{AB}$, corrected as discussed above, are supplied to the computation circuit. For example, the computation circuit may include a programmable microprocessor.

Figure 4:
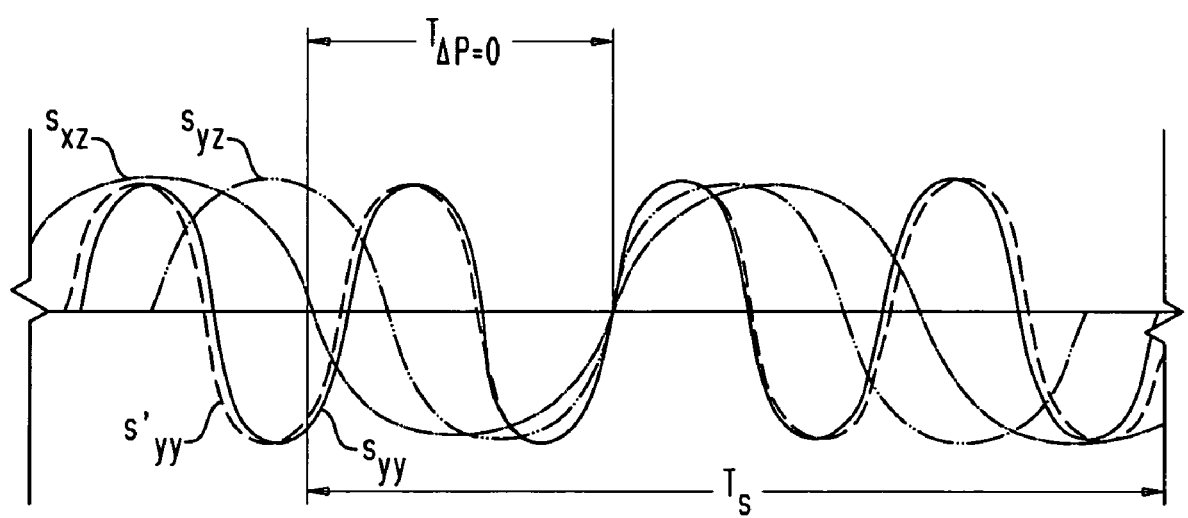
FIG. 4 is diagrammatic representation of certain signal components in the receiver used in the apparatus of FIG. 1.

The receiver uses a sampling interval having the same duration $T_S$ as the transmitter frame or sampling interval. However, the sampling interval $T_S$ of the receiver is not synchronized with the sampling interval of the transmitter. Thus, as shown in FIG. 4, the sampling interval $T_S$ of the receiver commences at an arbitrary time before the start of the sampling interval of the transmitter. However, as discussed above, the main frequency $f_Y$ and marker frequency $f'_Y$ used by the transmitter are aligned with one another only at the start of the sampling interval used by the transmitter. Therefore, the components $S_{YY}$ and $S'_{YY}$ derived from the sensor signals from receiver coil $30_Y$ will be aligned with one another at only at a time $T_{\Delta P=0}$ from the start of each sampling interval $T_S$ used by the receiver. Time $T_{\Delta P=0}$ in the sampling interval of the receiver corresponds to the start of the sampling interval used by the transmitter. Thus, by determining $T_{\Delta P=0}$, the receiver can determine the difference between its sampling interval and the sampling or frame interval of the transmitter.

The computation circuit 44 determines $T_{\Delta P=0}$ based on the main and marker frequency components in signals from one sensor coil, as, for example $S_{YY}$ and $S'_{YY}$. First, the sensor normalizes these components and determines the phase $P_Y$ of the component using the relationships:

$$Re(P_Y) = \frac{Re(S_{YY})}{\sqrt{Re(S_{YY})^2 + Im(S_{YY})^2}}$$

$$Im(P_Y) = \frac{Im(S_{YY})}{\sqrt{Re(S_{YY})^2 + Im(S_{YY})^2}}$$

$$Re(P'_Y) = \frac{Re(S'_{YY})}{\sqrt{Re(S'_{YY})^2 + Im(S'_{YY})^2}}$$

$$Im(P'_Y) = \frac{Im(S'_{YY})}{\sqrt{Re(S'_{YY})^2 + Im(S'_{YY})^2}}$$

The computation circuit then computes the phase difference $\Delta P$ at the beginning of the sampling interval $T_S$ used by the receiver using the relationship:

$$\Delta P = \frac{P_Y}{P'_Y}$$

evaluated at the beginning of the receiver sampling interval.

As the phase difference varies sinusoidally at a rate equal to the difference between $f_Y$ and $f'_Y$, and that rate is equal to the frame rate or $1/T_S$, the time $T_{\Delta P=0}$ is given by:

$$t_{\Delta P=0} = \frac{\tan^{-1}\left(\frac{Re(\Delta P)}{Im(\Delta P)}\right)}{2\pi(f_Y - f'_Y)}$$

The computation unit then calculates the phases $P_X$, $P_Y$ and $P_Z$ of the components at the main frequencies at the beginning of the sampling interval $T_S$ of the receiver using the relationships:

$Re(P_X)=\cos(-\omega_X t_{\Delta P=0})$ $Im(P_X)=\sin(-\omega_X t_{\Delta P=0})$ $Re(P_Y)=\cos(-\omega_Y t_{\Delta P=0})$ $Im(P_Y)=\sin(-\omega_Y t_{\Delta P=0})$ $Re(P_Z)=\cos(-\omega_Z t_{\Delta P=0})$ $Im(P_Z)=\sin(-\omega_Z t_{\Delta P=0})$ Where $\omega_X=2\Pi f_X$; $\omega_Y=2\Pi f_Y$; and $\omega_Z=2\Pi f_Z$.

Using these values, the computation unit forms an adjusted matrix of signal components, in which each component has been adjusted to equal the component as it would be if measured in synchronism with the transmitter. The adjusted matrix is as follows:

$$\begin{array}{ccc} \frac{S_{XX}}{j \cdot P_X} & \frac{S_{XY}}{j \cdot P_Y} & \frac{S_{XZ}}{j \cdot P_Z} \\ \frac{S_{YX}}{j \cdot P_X} & \frac{S_{YY}}{j \cdot P_Y} & \frac{S_{YZ}}{j \cdot P_Z} \\ \frac{S_{ZX}}{j \cdot P_X} & \frac{S_{ZY}}{j \cdot P_Y} & \frac{S_{ZZ}}{j \cdot P_Z} \end{array}$$

Stated another way, the receiver forms the adjusted matrix by deriving a phase-adjusted component $C_{AB}$ from each component $S_{AB}$ where $C_{AB}=S_{AB}/(j \cdot P_{1B})$ and $P_{1B}$ is the phase of the main component having frequency $f_B$ at the first point in the sampling period $T_S$ applied by the receiver. The adjusted matrix can also be written as:

$C_{XX} C_{XY} C_{XZ}$
$C_{YX} C_{YY} C_{YZ}$
$C_{ZX} C_{ZY} C_{ZZ}$

The computation unit derives the position and orientation of the receiver coils 30 in the frame of reference of the transmitter coils 10 from the adjusted matrix. The algorithm used to derive position and orientation from the adjusted matrix of components is conventional, and is described in the aforementioned U.S. Pat. No. 4,737,794. Briefly, the algorithm solves the matrix equation:

$$S = \frac{k}{r^3} A^T P H P^T M$$

where:
  S is a 3×3 signal matrix, which is the adjusted matrix described above;
  k is a constant incorporating system and calibration constants;
  r is the range of the sensor relative to the source;
  A is an attitude matrix, i.e., a 3×3 orthogonal matrix representative of the orientation of the sensor;
  P is a position matrix of 3 mutually orthogonal unit vectors, one of the unit vectors pointing toward the sensor from the source;
  H is a field coupling matrix;
  M is a source soil magnetic moment matrix; and
  the superscript "T" following a letter designating a matrix indicates the transpose of the matrix.

In this equation, there are two unknowns: r and A. All of the other components are known by design or measured during a calibration process. Since the attitude matrix A is orthogonal, the operation $S^T S$ (where T indicates the transpose) removes the orientation information, because multiplying an orthogonal matrix by its transpose yields a unity matrix. This allows the resulting equation to be solved for the range r. Then, the range r can be put back into the equation and used to solve the orientation matrix A.

The receiver is provided with an appropriate output device 46 for delivering the computed position and orientation. For example, the output device may be a radio transmitter for sending the position and orientation; a screen or other human-readable output device for indicating the position and orientation to a human user, or a link to some other electronic system for delivering the position and orientation in a format readable by such other system.

Numerous variations and combinations of the features described above can be used. For example, the main and marker frequencies may differ by more than one bin; the computations discussed above are adjusted accordingly. Also, the components used in determining $T_{\Delta P=0}$ may be derived from any one of the sensor coils. For example, the receiver may be arranged to select a particular sensor coil which has the strongest components at the main and marker frequencies, and to use the components from that sensor coil in the computation of $T_{\Delta P=0}$. Alternatively, the computation of $T_{\Delta P=0}$ may be repeated using components from each sensor coil and the results of these repetitions may be combined to provide a best estimate.

It is not essential that all of the main frequencies be synchronized with one another. If the phase relationships between the various main frequency signals applied to the transmitter coils are known, the system can compensate for these. In a further variant, the phase relationships between the main frequency signals may be unknown, and a marker frequency may be used with each main frequency to provide independent phase adjustment for each marker frequency.

In yet another variant, the receiver can use the measured timing offset or $T_{\Delta P=0}$ as an error signal, and adjust the timing of the receiver sampling interval $T_S$ to match the transmitter sampling interval $T_S$, i.e., to bring $T_{\Delta P=0}$ to zero. The matrix of components measured after the timing adjustment can be used without further phase adjustment. Timing adjustment may be performed at startup or intermittently.

Larger or smaller sets of transmitting and receiving coils can be used. For example, a two-dimensional locating system can use fewer coils. Also, the technique used to correct the marker-frequency and main-frequency components can be used in applications other than locating systems.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. Magnetic locating apparatus comprising:
  (a) a transmitter including a plurality of co-located orthogonal transmitter coils and a transmitter circuit operative to apply a signal to each transmitter coil including a main sinusoidal component having a frequency $f_B$, where B is an index denoting one of said transmitter coils, $f_B$ being different for different transmitter coils, the transmitter circuit also being operative to drive a particular one of the transmitter coils having a particular index B* with a sinusoidal marker component having a known amplitude and phase relationship to the main component transmitted by the same coil, the marker component having a frequency $f'_{B*}$ such that the difference between $f_{B*}$ and $f'_{B*}$ is smaller than the difference between any two of the main frequencies $f_B$;

(b) a receiver including a plurality of co-located orthogonal sensor coils to yield a plurality of sensor signals responsive to magnetic fields sent by the transmitter, the receiver including a receiver circuit operative to process the sensor signals to derive separate components $S_{AB}$ in each sensor signal at each main frequency $f_B$ where A is an index denoting one of the sensor coils and to derive a separate component $S'_{AB*}$ in at least one sensor signal at a marker frequency $f'_{B*}$, the receiver circuit also being operative to determine the phase of at least one component in at least one sensor signal from sensor signal components $S_{A*B*}$ and $S'_{A*B*}$, where A* is a particular value of A and to determine the position of the sensor coils relative to the transmitter coils based on the determined phase and on the components $S_{AB}$.

2. A system as claimed in claim 1 wherein the receiver circuit includes a correction circuit operative to correct the components $S_{A*B*}$ and $S'_{A*B*}$ based at least in part on a known relationship between the transmitted main and marker components from coil B*.

3. A system as claimed in claim 2 wherein the receiver circuit includes a sampling circuit to sample each sensor signal to provide time-domain data and a transformation circuit operative to transform the time-domain data to the frequency domain.

4. A system as claimed in claim 3 wherein the transformation circuit is operative to perform a discrete Fourier transform.

5. A system as claimed in claim 4 wherein the receiver circuit includes a windowing circuit operative to apply a weighting function to the time-domain data before the data is supplied to the transformation circuit, and wherein the correction circuit is operative to apply corrections based in part upon characteristics of the weighting function and the Fourier transform.

6. A system as claimed in claim 5 wherein the correction circuit is operative to apply the relationships:

$$S_{A*B*UNCORRECTED} = S_{A*B*CORRECTED} + K_1 (S'_{A*B*CORRECTED})$$

$$S'_{A*B*UNCORRECTED} = S'_{A*B*CORRECTED} + K_2 (S_{A*B*CORRECTED})$$

where K1 and K2 are constants.

7. A system as claimed in claim 3 wherein the receiver circuit is operative to sample the sensor signal components using a sampling period $T_S$ and wherein $f_{13} = n_B/T_S$ and $f'_B = n'_B/T_S$ where $n_B$ and $n'_B$ are integers.

8. A system as claimed in claim 7 wherein $n_{B*}$ and $n'_{B*}$ differ by one.

9. A system as claimed in claim 8 wherein the receiver circuit is operative to normalize the components $S_{A*B*}$ and $S'_{A*B*}$ to yield the phases $P_{A*B*}$ and $P'_{A*B*}$ at a known time in the sampling interval $T_S$ applied by the receiver, to calculate the phase difference at such known time $\Delta P_{A*B*} = (P_{A*B*}/P'_{A*B*})$ and to calculate a reference time $t_{\Delta P=0}$ at which $\Delta P_{A*B} = 0$ based on such phase difference.

10. A system as claimed in claim 9 wherein the transmitter circuit is operative to apply all of the main components with a known phase relationship to the main component sent by coil B*, and the receiver circuit is operative to calculate the phase $P_{1B}$ of each main component at the first point in the sampling period $T_S$ applied by the receiver based on $t_{\Delta P=0}$.

11. A system as claimed in claim 10 wherein the receiver circuit is operative to derive a phase-adjusted component $C_{AB}$ from each component $S_{AB}$ where $C_{AB} = S_{AB}/(j \cdot P_{1B})$ and to determine the position and orientation based on the phase-adjusted components.

12. A method of locating comprising the steps of:

(a) sending a plurality of magnetic signals from a plurality of co-located orthogonal transmitter coils, each of such signals including a main sinusoidal component having a different frequency $f_B$, where B is an index denoting one of said transmitter coils, the signal from a particular one of the transmitter coils having a particular index B* also including a sinusoidal marker component having a known amplitude and phase relationship to the main component transmitted by the same coil, the marker component having a frequency $f'_{B*}$ such that the difference between $f_{B*}$ and $f'_{B*}$ is smaller than the difference between any two of the main frequencies $f_B$;

(b) receiving the plurality of magnetic signals using a plurality of co-located orthogonal sensor coils to yield a plurality of sensor signals;

(c) processing the sensor signals to derive separate components $S_{AB}$ in each sensor signal at each main frequency $f_B$ where A is an index denoting one of the sensor coils and to derive a separate component $S'_{AB*}$ in at least one sensor signal at a marker frequency $f'_{B*}$;

(d) determining the phase of at least one component in at least one sensor signal from sensor signal components $S_{A*B*}$ and $S'_{A*B*}$, where A* is a particular value of A; and (e) determining the position of the sensor coils relative to the transmitter coils based on the determined phase and on the components $S_{AB}$.

13. A method as claimed in claim 12 wherein the processing step includes a step of correcting the components $S_{A*B*}$ and $S'_{A*B*}$ based at least in part on the known relationship between the transmitted main and marker components from coil B*.

14. A method as claimed in claim 13 wherein the step of processing the sensor signals includes sampling each sensor signal to provide time-domain data and transforming the time-domain data to the frequency domain.

15. A method as claimed in claim 14 wherein the step of transforming the time-domain data to the frequency domain includes performing a discrete Fourier transform.

16. A method as claimed in claim 15 further comprising the step of applying a weighting function to the time-domain data before performing the Fourier transform, wherein the correcting step is based in part upon characteristics of the weighting function and the Fourier transform.

17. A method as claimed in claim 16 wherein the step of correcting includes applying the relationships:

$$S_{A*B*UNCORRECTED} = S_{A*B*CORRECTED} + K_1 (S'_{A*B*CORRECTED})$$

$$S'_{A*B*UNCORRECTED} = S'_{A*B*CORRECTED} + K_2 (S_{A*B*CORRECTED})$$

where K1 and K2 are constants.

18. A method as claimed in claim 14 wherein the step of sampling is performed using a sampling period $T_s$ and wherein $f_B = n_B/T_s$ and $f'_B = n'_B/T_s$ where $n_B$ and $n'_B$ are integers.

19. A method as claimed in claim 18 wherein $n_{B*}$ and $n'_{B*}$ differ by one.

20. A method as claimed in claim 19 wherein the step of determining the phase includes normalizing the components $S_{A*B*}$ and $S'_{A*B*}$ to yield the phases $P_{A*B*}$ and $P'_{A*B*}$ at the beginning of the sampling interval $T_S$, calculating the phase difference $\Delta P_{A*B*} = (P_{A*B*}/P'_{A*B*})$ and calculating a reference time $t_{\Delta P=0}$ at which $\Delta P_{A*B*} = 0$.

21. A method as claimed in claim 20 wherein the main components sent by all of the coils have a known phase relationship to the main component sent by coil B*, the step of determining the position of the sensor coils including the step of calculating the phase $P_{1B}$ of each main components at the first point in the sampling period from $t_{\Delta P=0}$.

22. A method as claimed in claim 21 wherein the step of determining the position includes deriving a phase-adjusted component $C_{AB}$ from each component $S_{AB}$ where $C_{AB} = S_{AB}/(j \cdot P_{1B})$ and computing the position based on the phase-adjusted components.

23. A method of transmitting and receiving a sinusoidal signal including the steps of:
    (a) transmitting a composite signal including first and second sinusoidal components at first and second frequencies, said first and second sinusoidal components having a fixed phase and amplitude relationship;
    (b) receiving the composite signal;
    (c) sampling the received composite signal to provide time-domain data;
    (d) transforming the time-domain data to recover first and second recovered components; and
    (e) correcting the first and second recovered components based on the known relationships between the first and second components of said transmitted signal and known characteristics of the transformation to provide first and second corrected components at first and second frequencies.

24. A method as claimed in claim 23 further comprising the step of determining the phase of one of said corrected components based on the first and second corrected components.

25. A method as claimed in claim 24 wherein the sampling step is performed using a sampling time of duration Ts and said first and second frequencies are selected so that f=n/Ts and f'=n'/Ts where f is said first frequency, f' is said second frequency, and n and n' are different integers.

26. A method as claimed in claim 25 wherein f and f' differ by less than 5% of f.

27. A method as claimed in claim 26 wherein the transmitting step includes driving a resonant circuit including a coil with the composite signal so that the coil emits a magnetic field varying at the first and second frequencies.

28. A method as claimed in claim 25 wherein n and n' differ by one.

29. A method as claimed in claim 25 wherein the step of determining a phase includes determining a zero time corresponding to a zero phase of the first and second components, at which the instantaneous values of both components are crossing zero in the same preselected direction.

30. A method as claimed in claim 29 wherein the windowing function is a Blackman-Harris windowing function.

31. A method as claimed in claim 25 wherein the transformation step includes applying a windowing function to the sampled data in the time domain and subjecting the windowed time-domain data to a discrete Fourier transformation.

* * * * *

UNITED STATES PATENT AND TRADEMARK OFFICE
CERTIFICATE OF CORRECTION

PATENT NO. : 8,013,595 B2  Page 1 of 1
APPLICATION NO. : 12/157725
DATED : September 6, 2011
INVENTOR(S) : Herbert R. Jones, Robert F. Higgins and Henry E. Himberg It is certified that error appears in the above-identified patent and that said Letters Patent is hereby corrected as shown below:

In the Specifications:

Column 3, line 6, "circuit have" should read -- circuit must have --.
Column 4, line 42, "value unit circuit" should read -- value circuit --.
Column 5, line 11, "from one another by" should read -- by --.
Column 5, line 22, "to as frequency" should read -- to a frequency --.
Column 5, line 51, "$T_B$" should read -- $T_S$ --.
Column 7, line 7, "and outputs" should read -- and output --.
Column 7, lines 30-31, "which is actually a represents" should read -- which actually represents --.

In the Claims:

Column 11, line 54, "K1 and K2" should read -- $K_1$ and $K_2$ --.
Column 11, line 57, "where in $f_{13}$" should read -- wherein $f_B$ --.
Column 11, line 67, "$\Delta P_{A*B}$" should read -- $\Delta P_{A*B*}$ --.
Column 12, line 64, "K1 and K2" should read -- $K_1$ and $K_2$ --.
Column 13, line 14, "main components" should read -- main component --.
Column 14, line 13, "wherein f and f" should read -- wherein f and F --.

Signed and Sealed this
Thirteenth Day of August, 2013

Teresa Stanek Rea
*Acting Director of the United States Patent and Trademark Office*